(12) United States Patent
Rabinovitz et al.

(10) Patent No.: US 8,290,556 B2
(45) Date of Patent: Oct. 16, 2012

(54) DEVICE, SYSTEM AND METHOD FOR IN-VIVO ANALYSIS

(75) Inventors: Elisha Rabinovitz, Haifa (IL); Gavriel J. Iddan, Haifa (IL)

(73) Assignee: Given Imaging Ltd., Yoqneam (IL)

(*) Notice: Subject to any disclaimer, the term of this patent is extended or adjusted under 35 U.S.C. 154(b) by 1378 days.

(21) Appl. No.: 11/597,245

(22) PCT Filed: May 22, 2005

(86) PCT No.: PCT/IL2005/000525
§ 371 (c)(1),
(2), (4) Date: Nov. 7, 2007

(87) PCT Pub. No.: WO2005/113021
PCT Pub. Date: Dec. 1, 2005

(65) Prior Publication Data
US 2008/0064923 A1 Mar. 13, 2008

Related U.S. Application Data

(60) Provisional application No. 60/572,777, filed on May 21, 2004.

(51) Int. Cl.
*A61B 5/1455* (2006.01)

(52) U.S. Cl. .................. 600/310; 600/302; 600/476

(58) Field of Classification Search .................. 600/310, 600/317, 342, 473, 476, 100, 160
See application file for complete search history.

(56) References Cited

U.S. PATENT DOCUMENTS

| | | | |
|---|---|---|---|
| 4,278,077 A | 7/1981 | Mizumoto | |
| 5,604,531 A | 2/1997 | Iddan et al. | |
| 5,833,603 A | 11/1998 | Kovacs et al. | |
| 5,946,413 A * | 8/1999 | Shibata et al. | 382/174 |
| 5,993,378 A | 11/1999 | Lemelson | |
| 6,240,312 B1 | 5/2001 | Alfano et al. | |
| 6,303,081 B1 * | 10/2001 | Mink et al. | 422/412 |
| 6,365,417 B1 * | 4/2002 | Fleming et al. | 422/412 |
| 2002/0103417 A1 | 8/2002 | Gazdzinski | |

FOREIGN PATENT DOCUMENTS

| | | |
|---|---|---|
| DE | 344 0177 | 11/1984 |
| JP | 1992-144533 | 5/1992 |

OTHER PUBLICATIONS

International Search Report from International Application No. PCT/IL2005/000525 filed May 22, 2005.

* cited by examiner

*Primary Examiner* — Eric Winakur
(74) *Attorney, Agent, or Firm* — Pearl Cohen Zedek Latzer, LLP

(57) ABSTRACT

A device, system and method of in-vivo analysis. An in-vivo device may include a chromatography unit to interact in-vivo with a body lumen substance, and a sensor to sense in-vivo a property of the chromatography unit.

29 Claims, 5 Drawing Sheets

DEVICE, SYSTEM AND METHOD FOR IN-VIVO ANALYSIS

CROSS-REFERENCE TO RELATED APPLICATIONS

This application is a National Phase application of PCT International Application No. PCT/IL2005/000525, International Filing Date 22 May 2005, claiming priority of U.S. Provisional Application No. 60/572,777 filed 21 May 2004, all of which are hereby incorporated by reference in their entirety.

FIELD OF THE INVENTION

The present invention relates to in-vivo analysis in general, and to analysis using swallowable capsules in particular.

BACKGROUND OF THE INVENTION

An atypical concentration or presence of substances in body fluids or in body lumens may be indicative of the biological condition of the body. For example, the presence of elevated concentrations of red blood cells in the gastrointestinal (GI) tract may indicate different pathologies, depending on the location of the bleeding along the GI tract. Thus, for example, bleeding in the stomach may indicate an ulcer, whereas bleeding in the small intestine may indicate the presence of a tumor. Furthermore, different organs may contain different body fluids requiring different analysis methods. For example, the stomach secretes acids whereas pancreatic juice is basic.

Medical detection kits are usually based on in vitro testing of body fluid samples for the presence of a suspected substance. For example, in some cases, diseases, such as cancer, are detected by analyzing the blood stream for tumor specific markers, typically, specific antibodies. A drawback of this method is that the appearance of antibodies in the blood stream usually occurs at a late stage of the disease, such that early detection is not possible using this method. Furthermore, this method of detection does not easily allow localization or identification of the origin of a pathology.

Early detection, identification and location of abnormal conditions (such as, for example, an atypical presence or concentration of a substance) may be critical for definitive diagnosis and/or treating of various pathologies.

Devices, systems and methods for in-vivo sensing of passages or cavities within a body, and for sensing and gathering information (e.g., image information, pH information, temperature information, electrical impedance information, pressure information, etc.), are known in the art.

SUMMARY OF THE INVENTION

Various embodiments of the invention provide, for example, devices, systems and methods of in-vivo analysis.

In some embodiments, for example, an in-vivo device may include a chromatography strip or unit or element, to interact in-vivo with a body lumen substance, and an imager to acquire an in-vivo image of the chromatography strip.

In some embodiments, for example, the in-vivo device may include a chromatography unit to interact in-vivo with a body lumen substance; and a sensor to sense in-vivo a property (e.g., color, color intensity, color change, radiation, emitted signal, emitted radiation, change of a characteristic, or the like) of the chromatography unit. The sensor may be, for example, a photodiode, a photodiodes array, an electrochemical sensing unit, a magnetic field sensing unit, an imager, an image sensor, a light detector, a color detector, a light-sensitive unit, a color-sensitive unit, or the like.

In some embodiments, for example, the chromatography strip or unit is generally internal to the in-vivo device.

In some embodiments, for example, a portion of the chromatography strip or unit protrudes out of the in-vivo device to draw in a sample of the body lumen substance.

In some embodiments, for example, the chromatography strip or unit passes through a sleeve, a tube, a pipe, or other casing or housing for the strip.

In some embodiments, for example, the in-vivo device may include a sealing element or gate or plug to seal the entrance of the tube, and the body lumen substance can enter the tube only via the chromatography strip or unit. In some embodiments, the sealing element or gate or plug may be openable, for example, only if a pre-defined condition is met, at a specific time, at a specific location, or the like.

In some embodiments, for example, the chromatography strip or unit is attached to an external side of the in-vivo device.

In some embodiments, for example, the in-vivo device may include a housing having a substantially transparent portion, and the imager is able to acquire the in-vivo image through the housing portion.

In some embodiments, for example, the in-vivo device may include a coating insulating the chromatography strip or unit to reflect light emitted from the in-vivo device generally into the in-vivo device.

In some embodiments, for example, a portion of the chromatography strip or unit protrudes out of coating to draw in a sample of the body lumen substance.

In some embodiments, for example, at least a portion of the chromatography strip or unit is covered by a dissolvable plug.

In some embodiments, for example, the imager is to acquire an in-vivo image of a body lumen.

In some embodiments, for example, the in-vivo device may include an in-vivo camera to acquire an in-vivo image of a body lumen.

In some embodiments, for example, the in-vivo device may include a set of binding particles attached to a portion of the chromatography strip or unit.

In some embodiments, for example, the in-vivo device may include another set of binding particles attached to another portion of the chromatography strip or unit.

In some embodiments, for example, the in-vivo device may include a treatment compartment having a substance able to interact with a sample of the body substance collected by the chromatography strip or unit.

In some embodiments, for example, the in-vivo device may include a power source to apply an electric field to the chromatography strip or unit.

In some embodiments, for example, the in-vivo device may include a transmitter to transmit data of the in-vivo image.

In some embodiments, for example, a system may include the in-vivo device, an external receiver/recorder able to receive data (e.g., image data) transmitted by the in-vivo device, and a computing platform or workstation able to store, process, display, or analyze the received data.

Some embodiments of the invention may include a method of in-vivo analysis. The method may include, for example, acquiring an in-vivo image or obtaining other data such as calorimetric or intensity data, of a chromatography unit able to interact in-vivo with a body lumen substance; optionally, acquiring in-vivo an image of the body lumen; transmitting the acquired in-vivo image or other data of the chromatography unit; analyzing the in-vivo image or data of the chromatography unit; and/or other suitable operations.

Some embodiments may include, for example, an in-vivo imaging device which may be autonomous and/or may include a swallowable capsule.

Embodiments of the invention may allow various other benefits, and may be used in conjunction with various other applications.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings in which:

Figure 1A:
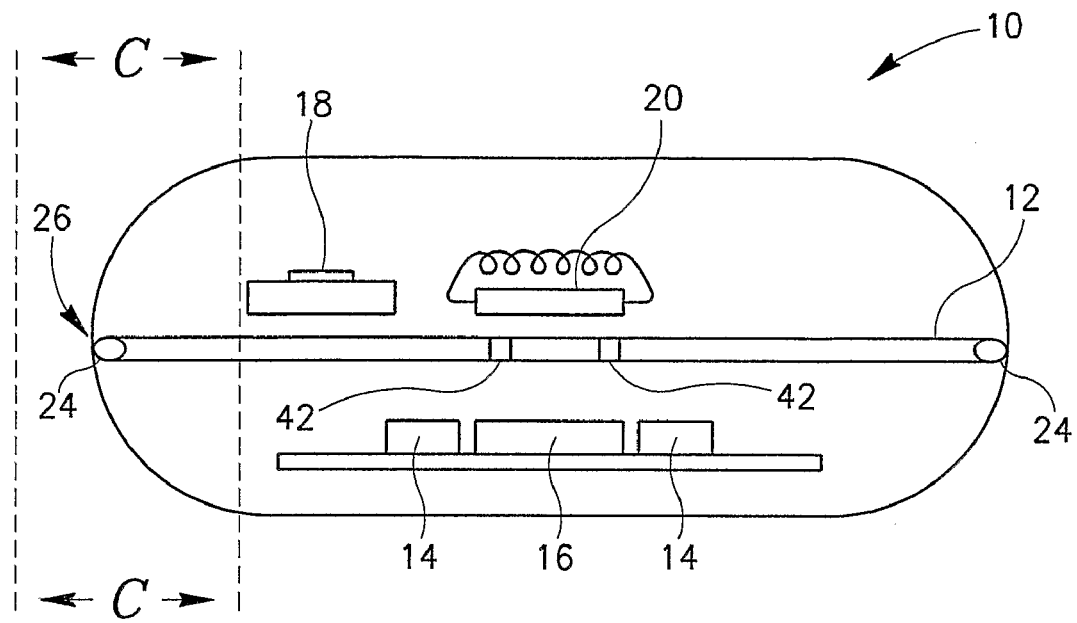
FIGS. 1A and 1B are schematic, cross section and longitudinal section illustrations of an in-vivo device, constructed and operative in accordance with an embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the invention will be described. For purposes of explanation, specific configurations and details are set forth in order to provide a thorough understanding of the invention. However, it will also be apparent to one skilled in the art that the invention may be practiced without the specific details presented herein. Furthermore, well-known features may be omitted or simplified in order not to obscure the invention.

It should be noted that although a portion of the discussion may relate to in-vivo imaging devices, systems, and methods, the present invention is not limited in this regard, and embodiments of the present invention may be used in conjunction with various other in-vivo sensing devices, systems, and methods. For example, some embodiments of the invention may be used, for example, in conjunction with in-vivo sensing of pH, in-vivo sensing of temperature, in-vivo sensing of pressure, in-vivo sensing of electrical impedance, in-vivo detection of a substance or a material, in-vivo detection of a medical condition or a pathology, in-vivo acquisition or analysis of data, and/or various other in-vivo sensing devices, systems, and methods. Some embodiments of the invention may be used not necessarily in the context of in-vivo imaging or in-vivo sensing.

Some embodiments of the present invention are directed to a typically swallowable in-vivo sensing device, e.g., a typically swallowable in-vivo imaging device. Devices according to embodiments of the present invention may be similar to embodiments described in U.S. patent application Ser. No. 09/800,470, entitled "Device And System For In-vivo Imaging", filed on 8 Mar., 2001, published on Nov. 1, 2001 as United States Patent Application Publication Number 2001/0035902, and/or in U.S. Pat. No. 5,604,531 to Iddan et al., entitled "In-vivo Video Camera System", and/or in International Application number WO 02/054932 entitled "System and Method for Wide Field Imaging of Body Lumens" published on Jul. 18, 2002, all of which are hereby incorporated by reference. An external receiving unit and processor, such as in a work station, such as those described in the above publications could be suitable for use with embodiments of the present invention. Devices and systems as described herein may have other configurations and/or other sets of components. For example, the present invention may be practiced using an endoscope, needle, stent, catheter, etc.

Figure 1B:
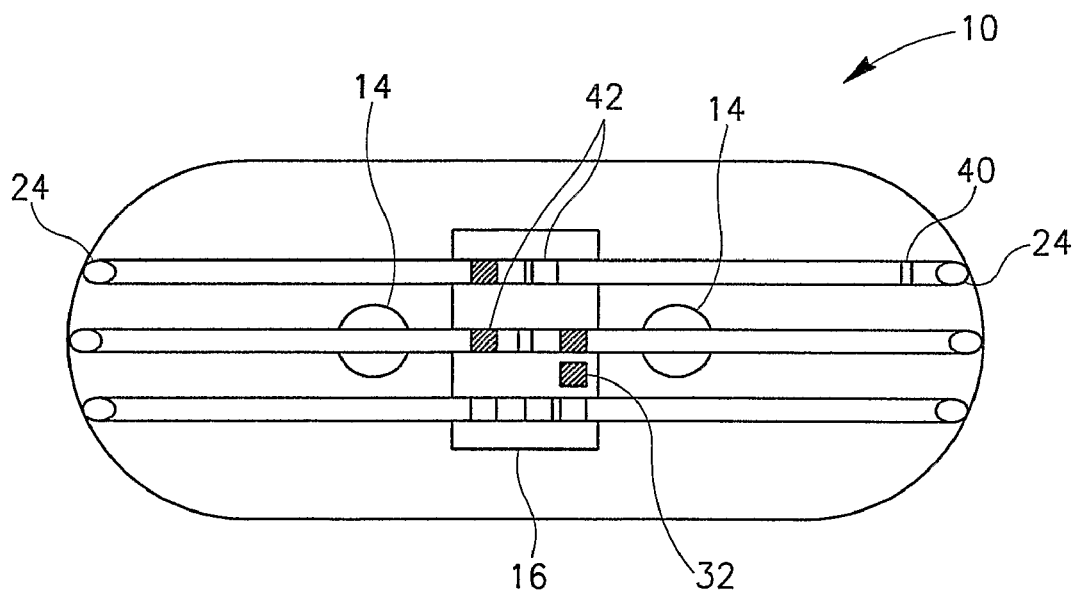

Reference is now made to FIGS. 1A and 1B, which depict an in-vivo device 10, for example, an autonomous in-vivo device, which may be a swallowable in-vivo device, or the like. According to one embodiment, the device may be capsule shaped. Device 10 may include one or more chromatography strips 12, or chromatography elements or units. The chromatography strips 12 need not be strip-shaped. Additionally, the device 10 may include an illumination source, such as Light-Emitting Diodes (LEDs) 14 or other suitable sources to illuminate strips 12 or portions of strip 12 and/or to illuminate a body lumen (or a portion thereof). Device 10 may further include a detector 16 to detect optical changes occurring on strips 12, and a transmitter 20 to transmit data (e.g., using wireless Radio Frequency (RF) signals) to an external receiving unit, for example, to transmit images taken of strips 12. Components of device 10 may receive power, for example, from a power source 18, e.g., a battery or power cell or wireless power receiving unit, which may be included in device 10.

Device 10 and other devices described herein typically may be, or may include, an autonomous swallowable capsule, but such devices may have other shapes and need not be swallowable and/or autonomous. Embodiments of the invention are typically autonomous, and are typically self-contained. For example, a device may be a capsule or other unit where all the components are substantially contained within a container or shell, and where device does not require any wires or cables to, for example, receive power or transmit information. The device may communicate with an external receiving and display system to provide display of data, control, or other functions. For example, power may be provided by an internal battery or a wireless receiving system. Other embodiments may have other configurations and capabilities. For example, components may be distributed over multiple sites or units. Control information may be received from an external source.

The chromatography strips or units 12 may be made of, for example, a pad or other support structure, such as a flat piece, or a unit of another shape, coated with or impregnated or otherwise including nitrocellulose or any other polymer suitable for a chromatographic process, and need not be strip shaped (e.g., if the flow is capillary creeping flow). In some embodiments, chromatographic assays, for example, testing for the presence and/or concentration of proteins, which may include antigens, antibodies, hormones and other proteins, lipids or other molecules whose presence or concentration may indicate abnormal conditions, may be performed on board in-vivo device 10. Other substances useful for detecting in-vivo substances may be used.

In some embodiments, chromatography strips or units 12 may be enclosed within sampling wells or chambers, or tubes or channels that may, for example, pass through the device 10. In one embodiment, the chromatography strips 12 may pass through the length of the wells. The device 10 may be inserted into a body lumen, for example, into a patient's GI tract, e.g., by swallowing. Fluid samples from the body lumen may enter the device 10, for example, at testing points 24, and the samples may progress along chromatography strips 12 according to predetermined properties, for example, as known in the art of chromatography. Testing point 24 may have a sealing element or gate (e.g., a passive gate or an active gate) that can be opened, for example, only under predetermined conditions.

Figure 1C:
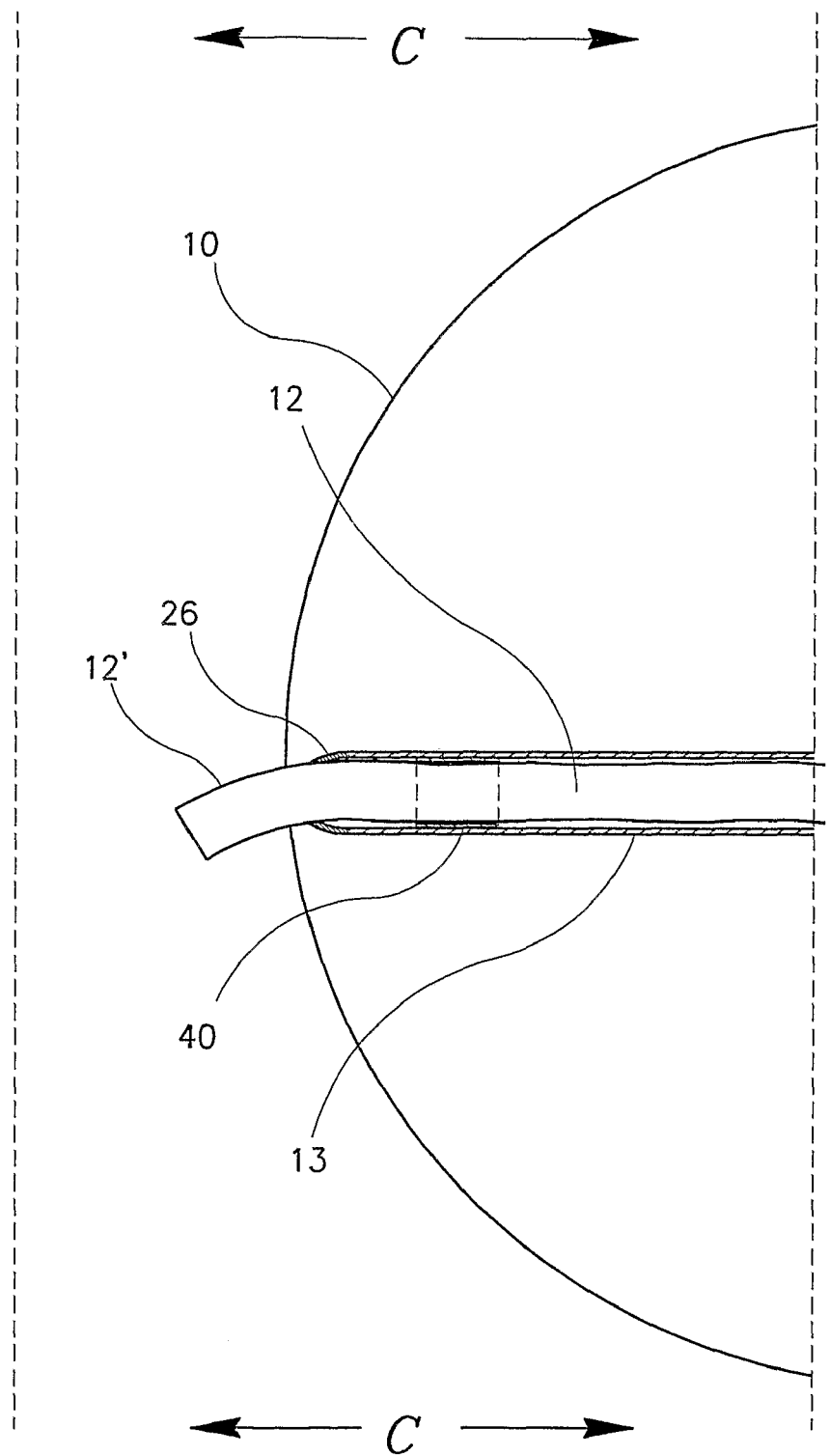
FIG. 1C is an enlargement along section C in FIG. 1A.

According to an embodiment of the invention, for example, as illustrated in FIG. 1C, one end 12' of chromatography strips 12 may protrude from a tube 13 (e.g., an insulating sleeve, a protecting sleeve, a supporting sleeve, a wrapping sleeve, a covering sleeve, a pipe, a cylinder, a cover, a casing, a coating, or the like) and may extend (or slightly extend) outside of device 10, such that the chromatography strip end 12' may come in contact with endo-luminal fluids outside of device 10. Endo-luminal fluids may thus be drawn in to tube 13, for example, due to the chromatographic or capillary properties of chromatographic strip 12. In one embodiment, to ensure that fluids enter tube 13 only via the chromatography strip 12, a sealing element or gate 26 can be fixed or used, e.g., at the entrance to tube 13. The tube 13 may, for example, wrap, support, hold and/or insulate the strip 12. The tube 13 may be, for example, substantially transparent or semi-transparent, e.g., to allow imaging of the strip 12 (or a portion thereof) through the tube 13.

Other suitable methods of drawing in endo-luminal samples may be used according to embodiments of the invention. For example, fluids may be drawn in due to capillary properties of tube 13. According to other embodiments, tube 13 may include a vacuumized compartment which may be used for drawing in fluids. Other suitable sampling methods may be used.

Along the tube 13, the sample may react with a first reactant or substance at an area 40, and the resultant fluid may continue to progress along chromatography strip 12. A second reaction may optionally occur at an area 42 (e.g., using an optional second reactant), which may be in view of detector 16, the second reaction resulting in a visible marking on chromatography strip 12. Indications of this reaction, such as optical changes or images of area 42 may be detected and/or imaged by detector 16, and may be transmitted by transmitter 20 to an external receiving unit. According to some embodiments, there may optionally be a calibration patch 32 on each strip 12 or in other suitable locations.

Detector 16 may include, for example, a photodiode, a fluorescence device, an electrochemical sensing device, a magnetic field sensing device, a spectrophotometer, an image sensor, a Charge Coupled Device (CCD) camera or imager, a Complementary Metal Oxide Semiconductor (CMOS) camera or imager, a digital camera, a stills camera, a video camera, or other suitable imagers, cameras, or image acquisition components.

In some embodiments, data collected or sensed by device 10 (e.g., images or image data) may be transmitted by transmitter 20 to an external receiver/recorder unit, which may be portable, non-portable, mobile, non-mobile, wearable, or the like. In one embodiment, the external receiver/recorder may include one or more antenna elements or an antenna array, e.g., to improve signal reception and/or to allow localization of the in-vivo device. The receiver/recorder may be operatively associated with a computing platform or workstation, which may, for example, store the received data (e.g., image data and/or other data), process the received data (e.g., using a processor), store the data in a storage unit, display the received data and/or processed data (e.g., using a monitor), analyze the data, perform post-processing operations, perform real-time processing operations, or the like.

In some embodiments, for example, the in-vivo device 10 may include the chromatography unit 12 to interact in-vivo with a body lumen substance; and a sensor (e.g., detector 16) to sense in-vivo a property (e.g., color, color intensity, color change, radiation, emitted signal, emitted radiation, change of a characteristic, or the like) of the chromatography unit 12. The sensor (e.g., detector 16) may be, for example, a photodiode, a photodiodes array, an electrochemical sensing unit, a magnetic field sensing unit, an imager, an image sensor, a light detector, a color detector, a light-sensitive unit, a color-sensitive unit, or the like.

Figure 2A:
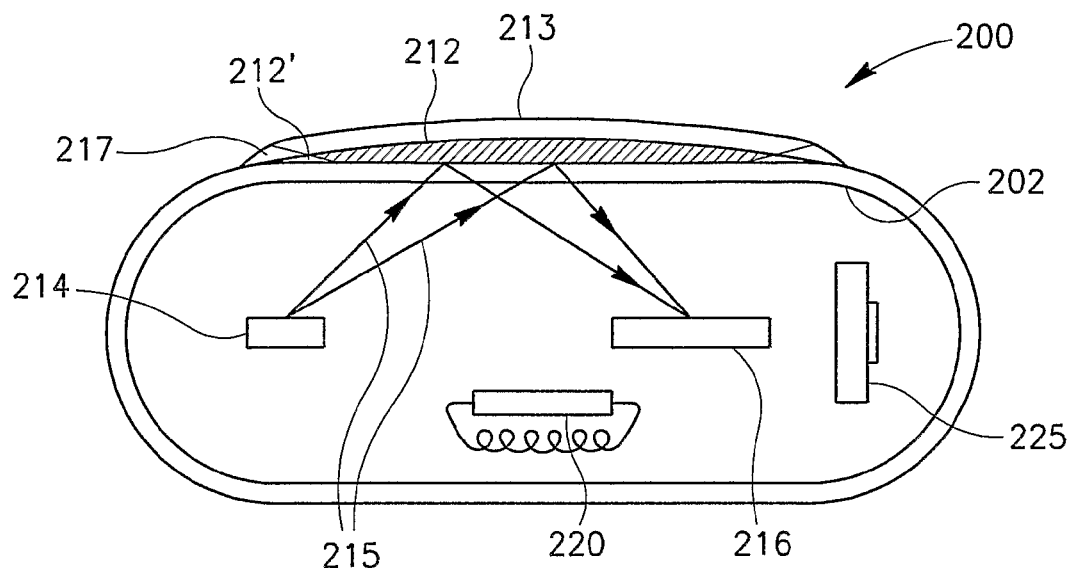
FIGS. 2A and 2B are schematic illustrations of an in-vivo device constructed and operative in accordance with another embodiment of the invention.

Reference is now made to FIG. 2A, a schematic illustration of an in-vivo device according to another embodiment of the invention. Device 200 may be configured to be inserted into a body lumen, such as into blood vessels, the urinary tract, the reproductive tract, the GI tract, or the like. For example, device 200 may be ovoid or capsule shaped such that it can be easily swallowed and moved through the GI tract by natural peristalsis, or guided through the GI tract or blood vessels using external force, e.g., magnetic fields.

A housing 202 of the device 200 is typically transparent so as to enable illumination from illumination source 214 to pass through the housing 202. According to one embodiment, a chromatography strip 212 may be placed directly on at least a portion of housing 202, on the external part of the housing 202. An insulating coating 213 may be placed directly over chromatography strip 212, for example, such that illumination from illumination source 214 (e.g., light rays 215) that is incident upon chromatography strip 212 will be mostly internally reflected into device 200.

The chromatography strip 212 may include, for example, a pad or other support structure, such as a flat piece, or a unit of another shape, coated with or impregnated or otherwise including nitrocellulose or any other polymer suitable for a chromatographic process. The insulating coating 213 may include any suitable material for isolating the chromatography strip 212 from the endo-luminal fluids. For example, the coating 213 may include plastics such as isplast (RTM), glass, or other typically biocompatible polymers, such as parylene, for example, parylene C. The chromatography strip 212 need not be "strip" shaped.

According to some embodiments, a tip 212' of the chromatography strip 212 may extend beyond the coating 213, such that it may be exposed to environment fluids and draw in a fluid sample. In one embodiment, the tip 212' may be covered by a plug 217 that may be positioned at one end of the coating 213. The plug 217, which serves as a gate, may be made of biodegradable or other disintegrating materials, such as carbohydrates, gelatin, wax, or the like. The plug 217 may serve to seal the tip 212' of chromatography strip 212 from body lumen fluids, while it is intact. According to some embodiments plug 217 may be disintegrated or otherwise perforated, such that tip 212' can come into contact with environmental fluids (e.g., body lumen fluids) and a fluid sample may be drawn into strip 212. The plug 217 may be disintegrated according to suitable methods, for example, in a time-dependant manner (e.g., according to the width or other, typically mechanical, properties of the plug 217), in a pH dependant manner, due to a specific enzymatic environment, due to specific prevailing bacteria or other fauna, in a temperature dependant manner, depending on a prevailing electromagnetic field, or the like.

Multiple strips 212 (and optionally, multiple associated plugs 217) may be used, for example, for obtaining duplicates, or for sampling a body lumen at more than one time point and/or in more than one location in the body lumen According to one embodiment, the device 200 may include a sensor 216 (e.g., an image sensor) and a transmitter 220 for transmitting data or images captured by sensor 216. A power source 225, such as a battery or a power unit based on RF power transmission, may be included to provide power to the components of the device 200. The illumination source 214 may include a white LED or a polychromatic LED or other suitable light source. The sensor 216 may include a light detector, a light sensor, a color sensor, a color detector, a CMOS imager or sensor, a CCD imager or detector, an imager, or any other suitable light intensity or image sensor.

Although portions of the discussion herein may relate to a chromatography unit which may be imaged in-vivo by an imager, embodiments of the invention are not limited in this regard; for example, instead of or in addition to an imager, a photodetector or light sensor may be used, e.g., a device capable of detecting or sensing one or more colors, intensities, hues, brightness, contrast, and/or other parameters or characteristic, a device sensitive to one or more colors or able to detect one or more colors, a device capable of detecting one or more color changes, a device sensitive to color changes, or the like. Such device, sensor or detector may be, but need not necessarily be, capable of acquiring an image of the chromatography unit(s) or a portion thereof.

In some embodiments, the illumination source 214 and/or the sensor 216 may be positioned relatively to the housing 202, such that each may be located on a focal point of the ellipsoid formed by the housing 202. This positioning of the illumination source 214 and/or the sensor 216 may ensure that internally reflected light will be incident mostly on the sensor 216, thereby enabling effective viewing of the chromatography strip 12 which may be positioned directly on the housing 202. According to other embodiments, the illumination source 214 and/or the sensor 216 may be positioned otherwise.

Figure 2B:
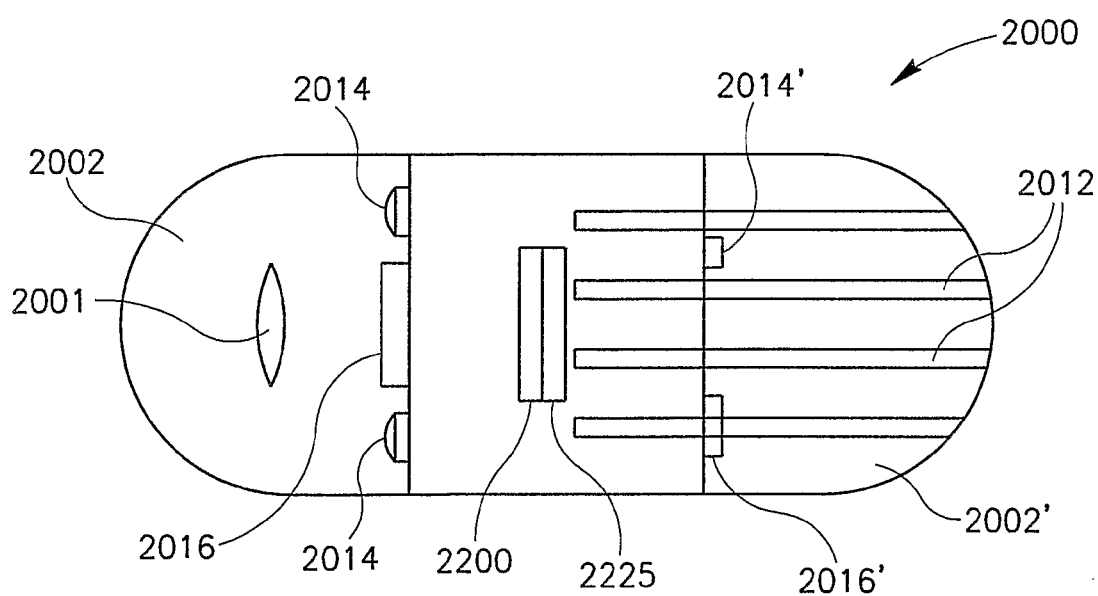

According to another embodiment, a schematic illustration of which is presented in FIG. 2B, an in-vivo device 2000 may be typically capsule shaped and may include at one end a dome 2002 which includes an image sensor 2016, light source(s) 2014 and an optical system 2001, all positioned behind the dome 2002. At another end of the device 2000 there may be a dome 2002', behind which are situated light source(s) 2014', an optional optical system, and an image sensor 2016'. Placed on the external surface of the dome 2002' may be chromatography strips 2012, for example as described with reference to FIG. 2A. Images of the body lumen captured, for example, by image sensor 2016, and/or images of the chromatography strips 2012 captured, for example, by image sensor 2016', may be transmitted to an external receiving unit by transmitter 2200. Alternatively, multiple different transmitters may be used for transmitting data from device 2000. The components of device 2000 may be powered by a power supply 2225.

In some embodiment, the optical system 2001 may include, for example, one or more lenses, mirrors, prisms, filters, gratings, or other optical elements. Optical system 2001 may, for example, direct, filter and/or focus light and/or illumination and/or light rays and/or reflected light, focus an image, focus the illumination source 2014 and/or the image sensor 2016 onto strip 2012, portion of strip 2012, portion of the body lumen, or the like, or the like. In one embodiment, deep field of focus may be used, for example, such that an image of the body lumen and the strip 2012 (or portion thereof) may be acquired by the image sensor 2016, the image having body lumen information coupled to strip 2012 information.

Figure 3:
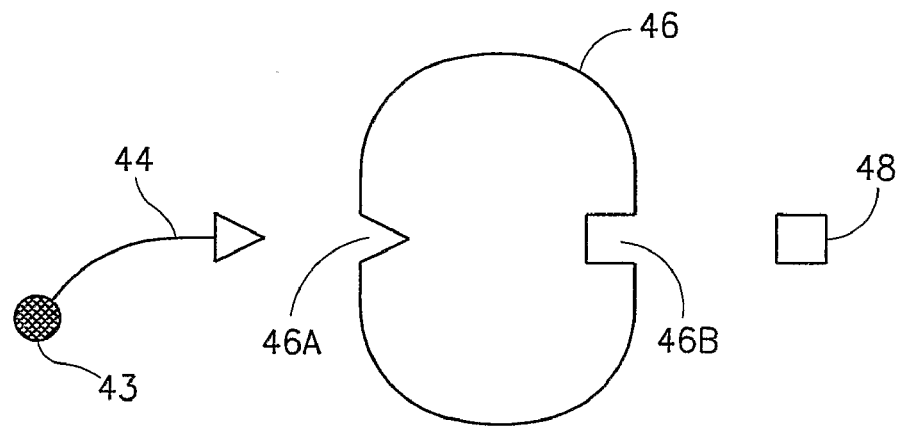
FIG. 3 is a schematic illustration of an exemplary reaction that may occur on a chromatographic testing strip, constructed in accordance with an embodiment of the present invention.

Reference is now made to FIG. 3, which depicts a reaction mechanism which may occur in chromatography strip 12 in accordance with an embodiment of the invention. Area 40 (FIGS. 1B and 1C), at a proximal end of strip 12, may contain first binding particles or substance 44. Area 42 (FIGS. 1A and 1B), at or near distal end of strip 12, may contain second binding particles or substance 48, e.g., bound or fixed or otherwise attached to the chromatography strip 12, the distal part of strip 12 after area 42 may serve as waste area. First substance 44 may be an antigen, antibody or other substance or molecules bound to or conjugated with a particle 43 that can be selected from a group consisting of colored particle, paramagnetic particle, radioactive particle or electrically charged particle. Fluids that have entered device 10 at testing point 24 (FIGS. 1A and 1B) may contain a substance such as a protein 46 (e.g. antigen, DNA or enzyme), which may have two or more binding sites 46A and 46B. In some embodiments, substance 44 and substance 48 may be configured to bind to sites 46A and 46B, respectively.

In some embodiments, if the fluid to be tested contains protein or substance 46, then as fluid passes through area 40 it may bind to a substance 44 at binding site 46A. Protein 46 bound to substance 44 may then progress together along chromatography strip 12 towards area 42.

In some embodiments, when bound substance 46 reaches area 42, it may bind with a substance 48 at binding site 46B. As substance 48 is fixed or attached to the strip 12 at area 42, there may be a multitude of protein or substance 46 gathered at area 42. The aggregation of many particles 46, which may be bound to particles 43 through substance 44 and 48, may show up as a patch on chromatography strip 12 at area 42. Particles 43 that are not bound to protein 46 will be washed away into the waste area.

It will be appreciated that, since the presence of particle 46 is noted by an aggregation of particle 43, the intensity of the signal (e.g., color or other property) of particle 43 may be proportional to the amount of particle 46 found in the fluid sample. For example, in one embodiment, particle 43 is colored, the intensity of the color at area 42 is proportional to substance 46, and sensor 16 may include a photodiode or imager or any detector sensitive to the specific color of particle 43. In another embodiment, particle 43 is made of radioactive material or a radiation-emitting material, and sensor 16 is a Geiger counter or any detector sensitive to the specific radiation.

According to one embodiment, the patch and possibly a calibration patch on strip 12 may be measured (or, for example, imaged, sensed, detected, or the like), and the measurements or calculated data may be transmitted, typically wirelessly, to a receiver/recorder outside a patient's body. The receiver/recorder may include a processor, or may be connected to a processor (e.g., in a workstation or computing platform), that may calculate a concentration or amount of substance 46 in a sample, based on the data of strip 12. For example, calorimetric parameters or spectral parameters, such as intensity, hue, brightness, saturation, contrast, histogram data, or the like, may be used to calculate or determine the concentration or amount of substance 46.

Calculations may be based on, or may include, comparison with a calibration patch and/or with a pre-defined reference value and/or a calculated reference value. Other suitable image processing techniques may be used.

In some embodiment, the processor may include, for example, a Central Processing Unit (CPU), a Digital Signal Processor (DSP), a microprocessor, a controller, a chip, a microchip, a controller, circuitry, an Integrated Circuit (IC), an Application-Specific Integrated Circuit (ASIC), or any other suitable multi-purpose or specific processor, controller, circuitry or circuit. In one embodiment, for example, the processing unit or controller may be embedded in or integrated with the transmitter, and may be implemented, for example, using an ASIC.

According to another embodiment, a processor on board the in-vivo device 10 may calculate or provide a quantitative determination of the particle 46. This information may be transmitted to a receiver outside the patient's body. Such processing may be preformed substantially in real-time or may be preformed offline, e.g., using post processing operations.

According to some embodiments, a software in, for example, the workstation that is configured to process and display image data received from the device 10, may give an automatic indication of the presence of a colored patch (for example, if the color in the image being viewed by an operator, is not discernible to the unassisted eye) and/or a quantitative determination, or other suitable indications.

In some embodiments, substance 46 may include, for example, tumor markers. Tumor markers may include molecules occurring in body fluid or tissue that are associated with cancer. Typically, tumor markers may be cancerous cells or products of cancerous cells, and may represent aberrant production of what may be a typically normal element. Some markers, such as antibodies, may be produced in response to the presence of cancer. Tumor marker targeted molecules may have a high affinity to tumor markers and, under certain conditions, may adhere to tumor markers in a liquid environment. These may include antigens having specificity to tumor marker antibodies. Alternatively, tumor marker targeted molecules may include antibodies specific to tumor marker antigens. Body fluid samples may be analyzed for other chemicals, compounds or molecules.

Figure 4:
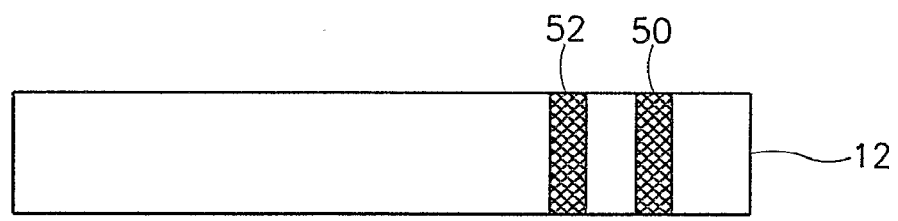
FIG. 4 is a schematic illustration of a chromatographic strip, constructed in accordance with an embodiment of the present invention.

In another embodiment of the present invention, as seen in FIG. 4, chromatography strip 12 may be pre-treated with a reagent that may react with a specific chemical, compound or molecule found in the fluid sample. Strip 12 may be pre-treated in two (or more) areas, for example, areas 50 and 52. Area 52 may be a calibration area, containing, for examples, particles capable of binding free particle 44 (which is bound to particle 43 but not bound to particle 46). Thus, a change (e.g., of color) in area 52 (typically due to particle 43) will occur in the presence of the fluid sample, regardless of whether or not the fluid sample contains the specific chemical, compound or molecule (e.g., particle 46) for which the sample is being tested. Moreover, as the number of binding particles in area 52 may be known, the intensity of the color (or other property or characteristic) or signal in area 52 can be related to a known concentration of particles 44. By comparing the intensity of the color (or other property or characteristic) or signal of area 52 to the intensity of the color (or other property or characteristic) or signal in area 50, the concentration of particles 46 can be determined. The second area 50 may include substances such as substances 48 that may bind substances 46, such that substances 46 (typically having particle 43 bound to it) may be aggregated at area 50 and may show up as an optical signal.

Figure 5:
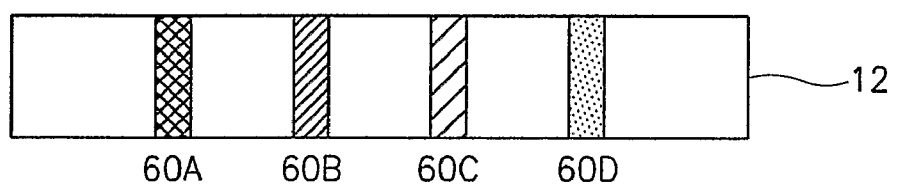
FIG. 5 is a schematic illustration of a strip, constructed in accordance with a further embodiment the present invention.

In yet another embodiment of the invention, chromatography strip 12 may be used (e.g., by the in-vivo device) to separate the testing fluid into many components. Reference is now made to FIG. 5, which depicts strip 12 used in a manner similar to a typical chromatography strip test. As fluid may move along strip 12, it may be separated into multiple components 60A-60D. For example, heavier components, such as components 60A, may stay towards the proximal end of strip 12, whereas lighter components, such as 60D, may advance and travel farthest, e.g., approaching the distal end of strip 12. A fluid sample may be treated (e.g., by passing through a treatment compartment at the entrance to strip 12), for example, to include a colored component such that components 60A-60D may appear on the strip 12 as color fronts at different locations along the strip 12. Various suitable chromatography methods may be used according to embodiments of the invention.

According to further embodiments of the invention, strip 12 may optionally include a matrix, such as a gel (e.g., agar, or the like), and an electric field may be applied to strip 12. In response, one or more components 60A-60D may be separated on strip 12 according to parameters such as, for example, size, weight, volume, electrical charge, conformation etc.

Figure 6:
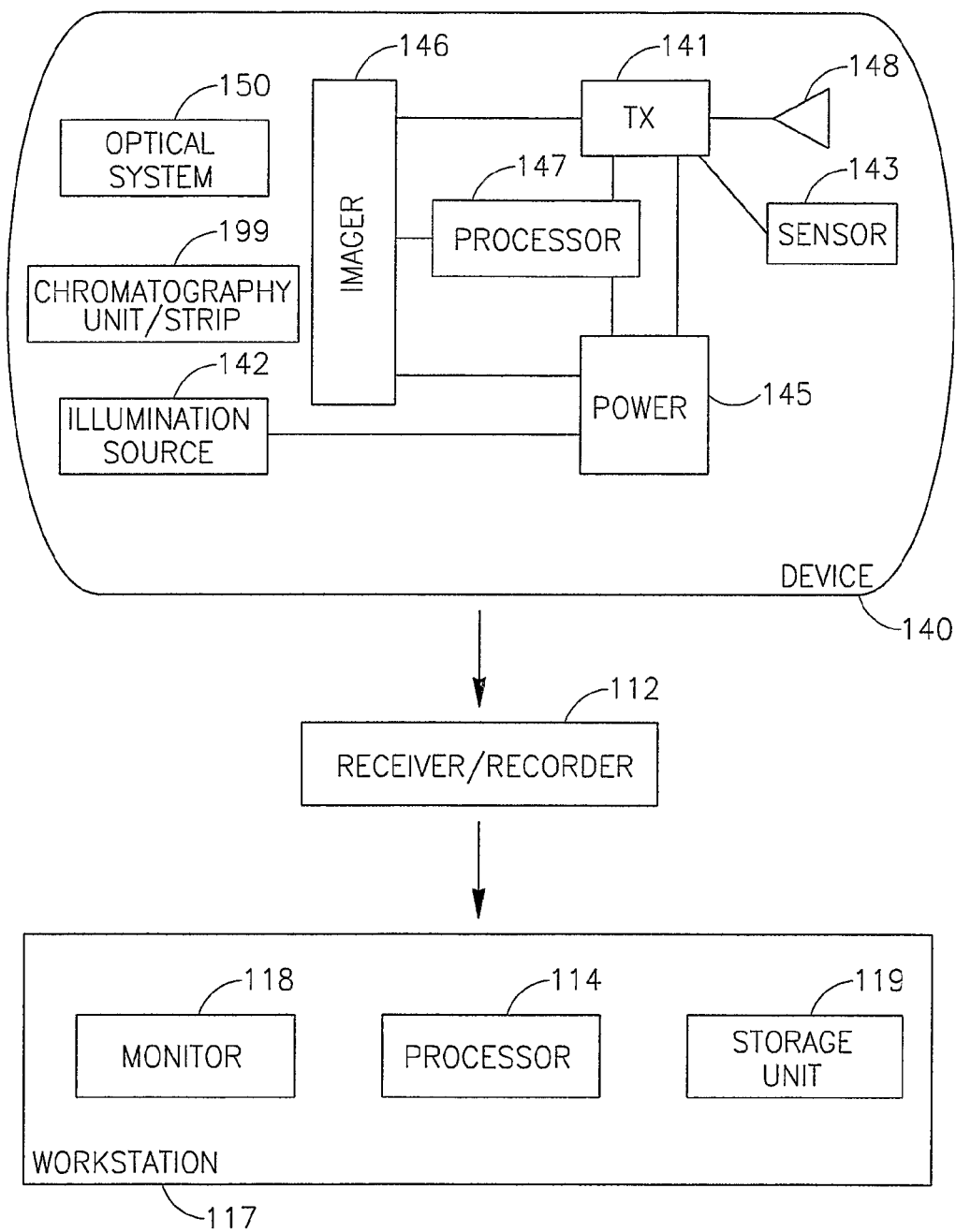
FIG. 6 is a schematic illustration of an in-vivo system in accordance with an embodiment of the present invention.

FIG. 6 shows a schematic illustration of an in-vivo system in accordance with some embodiments of the present invention. One or more components of the system may be used in conjunction with, may be operatively associated with, or may be included in, the device 10 of FIGS. 1A and 1B, the device 200 of FIG. 2A, the device 2000 of FIG. 2B, or other in-vivo devices in accordance with embodiments of the invention.

In one embodiment, the system may include a device 140 having a sensor, e.g., an imager 146, one or more illumination sources 142, a power source 145, and a transmitter 141. In some embodiments, device 140 may be implemented using a swallowable capsule, but other sorts of devices or suitable implementations may be used. Outside a patient's body may be, for example, an external receiver/recorder 112 (including, or operatively associated with, for example, an antenna or an antenna array), a storage unit 119, a processor 114, and a monitor 118. In one embodiment, for example, processor 114, storage unit 119 and/or monitor 118 may be implemented as a workstation 117, e.g., a computer or a computing platform.

Transmitter 141 may operate using radio waves; but in some embodiments, such as those where device 140 is or is included within an endoscope, transmitter 141 may transmit/receive data via, for example, wire, optical fiber and/or other suitable methods. Other known wireless methods of transmission may be used. Transmitter 141 may include, for example, a transmitter module or sub-unit and a receiver module or sub-unit, or an integrated transceiver or transmitter-receiver.

Device 140 typically may be or may include an autonomous swallowable capsule, but device 140 may have other shapes and need not be swallowable or autonomous. Embodiments of device 140 are typically autonomous, and are typically self-contained. For example, device 140 may be a capsule or other unit where all the components are substantially contained within a container or shell, and where device 140 does not require any wires or cables to, for example, receive power or transmit information. In one embodiment, device 140 may be autonomous and non-remote-controllable; in another embodiment, device 140 may be partially or entirely remote-controllable.

In some embodiments, device 140 may communicate with an external receiving and display system (e.g., workstation 117 or monitor 118) to provide display of data, control, or other functions. For example, power may be provided to device 140 using an internal battery, an internal power source, or a wireless system able to receive power. Other embodiments may have other configurations and capabilities. For example, components may be distributed over multiple sites or units, and control information or other information may be received from an external source.

In one embodiment, device 140 may include an in-vivo video camera, for example, imager 146, which may capture and transmit images of, for example, the GI tract while device 140 passes through the GI lumen. Other lumens and/or body cavities may be imaged and/or sensed by device 140. In some embodiments, imager 146 may include, for example, a Charge Coupled Device (CCD) camera or imager, a Complementary Metal Oxide Semiconductor (CMOS) camera or imager, a digital camera, a stills camera, a video camera, or other suitable imagers, cameras, or image acquisition components.

In one embodiment, imager 146 in device 140 may be operationally connected to transmitter 141. Transmitter 141 may transmit images to, for example, external transceiver or receiver/recorder 112 (e.g., through one or more antennas), which may send the data to processor 114 and/or to storage unit 119. Transmitter 141 may also include control capability, although control capability may be included in a separate component, e.g., processor 147. Transmitter 141 may include any suitable transmitter able to transmit image data, other sensed data, and/or other data (e.g., control data) to a receiving device. Transmitter 141 may also be capable of receiving signals/commands, for example from an external transceiver. For example, in one embodiment, transmitter 141 may include an ultra low power Radio Frequency (RF) high bandwidth transmitter, possibly provided in Chip Scale Package (CSP).

In some embodiment, transmitter 141 may transmit/receive via antenna 148. Transmitter 141 and/or another unit in device 140, e.g., a controller or processor 147, may include control capability, for example, one or more control modules, processing module, circuitry and/or functionality for controlling device 140, for controlling the operational mode or settings of device 140, and/or for performing control operations or processing operations within device 140. According to some embodiments, transmitter 141 may include a receiver which may receive signals (e.g., from outside the patient's body), for example, through antenna 48 or through a different antenna or receiving element. According to some embodiments, signals or data may be received by a separate receiving device in device 140.

Power source 145 may include one or more batteries or power cells. For example, power source 145 may include silver oxide batteries, lithium batteries, other suitable electrochemical cells having a high energy density, or the like. Other suitable power sources may be used. For example, power source 145 may receive power or energy from an external power source (e.g., an electromagnetic field generator), which may be used to transmit power or energy to in-vivo device 140.

Optionally, in one embodiment, transmitter 141 may include a processing unit or processor or controller, for example, to process signals and/or data generated by imager 146. In another embodiment, the processing unit may be implemented using a separate component within device 140, e.g., controller or processor 147, or may be implemented as an integral part of imager 146, transmitter 141, or another component, or may not be needed. The processing unit may include, for example, a Central Processing Unit (CPU), a Digital Signal Processor (DSP), a microprocessor, a controller, a chip, a microchip, a controller, circuitry, an Integrated Circuit (IC), an Application-Specific Integrated Circuit (ASIC), or any other suitable multi-purpose or specific processor, controller, circuitry or circuit. In one embodiment, for example, the processing unit or controller may be embedded in or integrated with transmitter 141, and may be implemented, for example, using an ASIC.

In some embodiments, device 140 may include one or more illumination sources 142, for example one or more Light Emitting Diodes (LEDs), "white LEDs", or other suitable light sources. Illumination sources 142 may, for example, illuminate a body lumen or cavity being imaged and/or sensed. An optional optical system 150, including, for example, one or more optical elements, such as one or more lenses or composite lens assemblies, one or more suitable optical filters, or any other suitable optical elements, may optionally be included in device 140 and may aid in focusing reflected light onto imager 146, focusing illuminated light, and/or performing other light processing operations.

Data processor 114 may analyze the data received via external receiver/recorder 112 from device 140, and may be in communication with storage unit 119, e.g., transferring frame data to and from storage unit 119. Data processor 114 may provide the analyzed data to monitor 118, where a user (e.g., a physician) may view or otherwise use the data. In one embodiment, data processor 114 may be configured for real time processing and/or for post processing to be performed and/or viewed at a later time. In the case that control capability (e.g., delay, timing, etc) is external to device 140, a suitable external device (such as, for example, data processor 114 or external receiver/recorder 112 having a transmitter or transceiver) may transmit one or more control signals to device 140.

Monitor 118 may include, for example, one or more screens, monitors, or suitable display units. Monitor 118, for example, may display one or more images or a stream of images captured and/or transmitted by device 140, e.g., images of the GI tract or of other imaged body lumen or cavity. Additionally or alternatively, monitor 118 may display, for example, control data, location or position data (e.g., data describing or indicating the location or the relative location of device 140), orientation data, and various other suitable data. In one embodiment, for example, both an image and its position (e.g., relative to the body lumen being imaged) or location may be presented using monitor 118 and/or may be stored using storage unit 119. Other systems and methods of storing and/or displaying collected image data and/or other data may be used.

Typically, device 140 may transmit image information in discrete portions. Each portion may typically correspond to an image or a frame; other suitable transmission methods may be used. For example, in some embodiments, device 140 may capture and/or acquire an image once every half second, and may transmit the image data to external receiver/recorder 112. Other constant and/or variable capture rates and/or transmission rates may be used.

Typically, the image data recorded and transmitted may include digital color image data; in alternate embodiments, other image formats (e.g., black and white image data) may be used. In one embodiment, each frame of image data may include 256 rows, each row may include 256 pixels, and each pixel may include data for color and brightness according to known methods. For example, a Bayer color filter may be applied. Other suitable data formats may be used, and other suitable numbers or types of rows, columns, arrays, pixels, sub-pixels, boxes, super-pixels and/or colors may be used.

Optionally, device 140 may include one or more sensors 143, instead of or in addition to a sensor such as imager 146. Sensor 143 may, for example, sense, detect, determine and/or measure one or more values of properties or characteristics of the surrounding of device 140. For example, sensor 143 may include a pH sensor, a temperature sensor, an electrical conductivity sensor, a pressure sensor, or any other known suitable in-vivo sensor.

Device 140 may further include one or more components or mechanisms of the device 10 of FIGS. 1A and 1B, of the device 200 of FIG. 2A, of the device 2000 of FIG. 2B, and/or of other in-vivo devices in accordance with embodiments of the invention. Such components may include, for example, one or more chromatography strips or units (e.g., chromatography unit 199), internal chromatography strips or units, external chromatography strips or units, plugs, dissolvable plugs, wells, tubes, sampling chambers, sealing elements, insulating coatings, multiple imagers, or other suitable components.

Some embodiments of the invention may include a method of in-vivo analysis. The method may include, for example, acquiring an in-vivo image of a chromatography unit able to interact in-vivo with a body lumen substance; optionally, acquiring in-vivo an image of the body lumen; transmitting the acquired in-vivo image of the chromatography unit; analyzing the in-vivo image of the chromatography unit; and/or other suitable operations.

Various aspects of the various embodiments disclosed herein are combinable with the other embodiments disclosed herein.

Although portions of the discussion herein may relate to chromatography "strips", embodiments of the invention are not limited in this regard, and may include, for example, chromatography units, chromatography elements, chromatography components, chromatography testers, or the like, which may be strip-shaped, non strip-shaped, or may have various suitable shapes and dimensions.

Although portions of the discussion herein may relate to collection and/or release of fluid or body fluid, the present invention is not limited in this regard, and may include, for example, collection and/or release of one or more materials, substances, fluids, solids, gases, materials including both fluids and solids, or the like.

Although portions of the discussion herein may relate to an imager or an image sensor, embodiments of the invention are not limited in this regard; such imager or image sensor may include, for example, a detector, a sensor, a photodiode, a fluorescence device, an electrochemical sensing device, a magnetic field sensing device, a spectrophotometer, an image sensor, a Charge Coupled Device (CCD) camera or imager, a Complementary Metal Oxide Semiconductor (CMOS) camera or imager, a digital camera, a stills camera, a video camera, a light sensor; a device capable of detecting or sensing one or more colors, intensities, hues, brightness, contrast, and/or other parameters or characteristic; a device sensitive to one or more colors or able to detect one or more colors; a device capable of detecting one or more color changes; a device sensitive to color changes; or the like A device, system and method in accordance with some embodiments of the invention may be used, for example, in conjunction with a device which may be inserted into a human body. However, the scope of the present invention is not limited in this regard. For example, some embodiments of the invention may be used in conjunction with a device which may be inserted into a non-human body or an animal body.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An in-vivo device comprising;
a swallowable capsule;
a chromatography unit configured to interact in-vivo with a body lumen substance; and
a sensor to sense in-vivo a property of said chromatography unit.

2. The in-vivo device of claim 1, wherein said chromatography unit is generally internal to the swallowable capsule.

3. The in-vivo device of claim 2, wherein a portion of said chromatography unit protrudes out of the swallowable capsule to draw in a sample of said body lumen substance.

4. The in-vivo device of claim 1, wherein said chromatography unit passes through a tube.

5. The in-vivo device of claim 4, wherein said tube is substantially transparent.

6. The in-vivo device of claim 4, comprising a sealing element to seal the entrance of said tube, and wherein said tube is able to receive said body lumen substance only via said chromatography unit.

7. The in-vivo device of claim 4, comprising a sealing element to seal the entrance of said tube, and wherein said sealing element is openable if a pre-defined condition is met.

8. The in-vivo device of claim 1, wherein said chromatography unit is attached to an external side of said swallowable capsule.

9. The in-vivo device of claim 1, said swallowable capsule further comprising a housing having a substantially transparent portion, and wherein said sensor is configured to sense said property through said housing portion.

10. The in-vivo device of claim 9, comprising a coating insulating said chromatography unit to reflect light emitted from said in-vivo device generally into said in-vivo device.

11. The in-vivo device of claim 10, wherein a portion of said chromatography unit protrudes out of said coating to draw in a sample of said body lumen substance.

12. The in-vivo device of claim 9, wherein at least a portion of said chromatography unit is covered by a dissolvable plug.

13. The in-vivo device of claim 1, wherein said sensor comprises an in-vivo imager to acquire an image of at least a portion of said chromatography unit.

14. The in-vivo device of claim 1, wherein said sensor is selected from the group consisting of: a photodiode, a photodiodes array, an electrochemical sensing unit, and a magnetic field sensing unit.

15. The in-vivo device of claim 1, comprising an in-vivo camera to acquire an in-vivo image of a body lumen.

16. The in-vivo device of claim 1, comprising a set of binding particles attached to a portion of said chromatography unit.

17. The in-vivo device of claim 16, comprising another set of binding particles attached to another portion of said chromatography unit.

18. The in-vivo device of claim 1, comprising a treatment compartment having a substance able to interact with a sample of said body lumen substance collected by said chromatography unit.

19. The in-vivo device of claim 1, comprising a power source to apply an electric field to said chromatography unit.

20. The in-vivo device of claim 1, comprising:
a transmitter to transmit the sensed data.

21. The in-vivo device of claim 1, wherein said chromatography unit comprises at least one chromatography strip.

22. The in-vivo device of claim 1, wherein said in-vivo device is autonomous.

23. A system comprising:
    an in-vivo device comprising at least a swallowable capsule, a chromatography unit configured to interact in-vivo with a body lumen substance, and an imager to image in-vivo a property of said chromatography unit; and
    a receiver to receive image data from said in-vivo device.

24. The system of claim 23, wherein said in-vivo device comprises a transmitter to transmit said image data.

25. The system of claim 23, wherein said in-vivo device comprises an in-vivo camera to acquire an image of a body lumen.

26. A method comprising:
    swallowing an in-vivo device, said in-vivo device comprising a swallowable capsule, a chromatography unit configured to interact in-vivo with a body lumen substance and an imager; and
    acquiring an in-vivo image of said chromatography unit in-vivo.

27. The method of claim 26, comprising:
    acquiring in-vivo an image of said body lumen.

28. The method of claim 26, comprising:
    transmitting the acquired in-vivo image of said chromatography unit.

29. The method of claim 26, comprising:
    analyzing said in-vivo image of said chromatography unit.

* * * * *